(12) United States Patent
Pieroni et al.

(10) Patent No.: US 7,842,679 B2
(45) Date of Patent: Nov. 30, 2010

(54) PHOSPHOLIPID DERIVATIVES OF DHA AND METHODS FOR TREATING RESPIRATORY FAILURE USING THE SAME

(76) Inventors: Gérard Pieroni, 40 boulevard Vauban, F-13006 Marseilles (FR); Thierry Coste, 3 Avenue Paul Garnier, Impasse des Fauvettes, F-13390 Auriol (FR)

(*) Notice: Subject to any disclaimer, the term of this patent is extended or adjusted under 35 U.S.C. 154(b) by 0 days.

(21) Appl. No.: 12/040,958

(22) Filed: Mar. 3, 2008

(65) Prior Publication Data

US 2008/0160066 A1    Jul. 3, 2008

Related U.S. Application Data

(63) Continuation of application No. PCT/FR2006/001988, filed on Aug. 25, 2006.

(30) Foreign Application Priority Data

Sep. 1, 2005    (FR) .................... 05 08956

(51) Int. Cl.
*A01N 57/26*    (2006.01)
(52) U.S. Cl. .................... 514/78; 424/456; 424/464; 424/440
(58) Field of Classification Search ............ 424/440, 424/456, 464; 514/78
See application file for complete search history.

(56) References Cited

U.S. PATENT DOCUMENTS 7,074,389 B2 *   7/2006   Frankenberger et al. ....... 424/45

FOREIGN PATENT DOCUMENTS

| FR | 2 749 133 | * | 6/1996 |
| JP | 05-043456 | * | 2/1993 |
| WO | WO 02094283 | * | 11/2002 |

OTHER PUBLICATIONS

Hashimoto et al., {1-Oleoyl-2-docosahexaenoyl phosphatidylcholine increased paradoxical sleep in F344 rats, Neuroscience letters 158, 1993, 29-32}.*

* cited by examiner

*Primary Examiner*—Daniel M Sullivan
*Assistant Examiner*—Chukwuma O Nwaonicha
(74) *Attorney, Agent, or Firm*—Matthias Scholl, PC; Matthias Scholl

(57) ABSTRACT

Taught are pharmaceutical compositions comprising at least one phospholipid having at least one docosahexaenoyl (DHA) residue, such as a lecithin-DHA-type phospholipid, and methods for treating or preventing respiratory failure of a patient comprising administering these pharmaceutical compositions to a patient in need of such treatment or prevention.

15 Claims, No Drawings

PHOSPHOLIPID DERIVATIVES OF DHA AND METHODS FOR TREATING RESPIRATORY FAILURE USING THE SAME

CROSS-REFERENCE TO RELATED APPLICATIONS

This application is a continuation of International Patent Application No. PCT/FR2006/001988 with an international filing date of Aug. 25, 2006, designating the United States, now pending, and further claims priority benefits to French Patent Application No. 0508956, filed Sep. 1, 2005. The contents of the aforementioned specifications are incorporated herein by reference.

BACKGROUND OF THE INVENTION

1. Field of the Invention

This invention relates to the field of medicine, and more particularly to pharmaceutical compositions and methods for the treatment and prevention of respiratory failure.

2. Description of the Related Art

Living things derive their energy from their surroundings. They remove from their environment substances rich in nutrients or energy, degrading them in the process, and rejecting the remains of the degradation process. Respiration is essential for life. The cells of our body consume oxygen ($O_2$) and emit carbon dioxide ($CO_2$). The respiratory system is responsible for carrying out the gaseous exchange between the organism (the blood) and the surrounding atmosphere. The blood transports the gas between the respiratory system and the cells.

The respiratory system is comprised of two principal elements: a respiratory pump (ribcage, respiratory muscle) intended, like bellows, to take in and let out air from the lungs; and a gas diffuser (airways, lungs) which, on an air cell level, performs the $O_2$—$CO_2$ exchange between the blood and the alveolar air.

Respiratory failure is defined as the incapacity of the respiratory system to perform its role, that is to say to maintain normal hematose (transformation of venous blood, rich in $CO_2$, to arterial blood, rich in $O_2$). It can be chronic (slow onset) or acute (sudden onset).

Respiratory failure can have different causes. There are three known major categories of respiratory failure: obstructive syndromes (bronchitis, asthma, cystic fibrosis, etc.); restrictive syndromes (neuromuscular ailments, scolioses, motor disability, excess weight, etc.); and mixed syndromes.

Currently, curative treatment for respiratory failure, besides the treatment of obstructive syndromes by bronchodilators, calls primarily upon mechanical breathing equipment and/or on the supply of oxygen in the case of substantial bronchiole congestion.

All of the proposed solutions therefore refer to processes aimed at increasing the oxygen supply to the body. For example, Japanese Pat. Appl. Publ. No. JP 11-29410 published on Feb. 2, 1999 describes the use of DHA phospholipids for administration in the form of an aerosol, in the treatment of lung disease during acute attacks. The described treatment is not suitable for the long term and is aimed only at improving the oxygen supply to the body in the short term.

Another of the processes described in the art, is aimed at improving the oxygen uptake and its transport in the body by the blood, particularly in the long term.

Currently, no medicine exists which is aimed specifically at the symptomatic prevention of respiratory failure in humans, with proven effectiveness and harmlessness.

It is known that long-chain n-3 fatty acids (n-3 LC-PUFA) such as eicosapentaenoic acid (EPA; 20:5n-3) and docosahexaenoic acid (DHA; 22:6n-3) have multiple effects on cell membranes, in particular, the fluidity of the red corpuscle membranes, and that they are equally likely to act on the vascular contractability and the cardiac rhythm. Thus, the oxygen supply to the body depends on the hemoviscosity, which is linked to the deformability, of the red corpuscles, and on the vasodilatation of the vessels which regulate the peripheral micro-circulation.

The n-3 LC-PUFA are therefore potential agents capable of modulating the oxygenation of tissues and, therefore, of respiration.

It has thus been shown that a daily intake of 3 g of n-3 LC-PUFA (1.8 g of EPA and 1.2 g of DHA) in the form of fish oil, that is to say a dose much higher than the maximum limit of 2 g/day of n-3 LC-PUFA recommended by the AFSSA (Agence Française pour la Sécurité Sanitaire des Aliments–French Food Standards Agency), leads to an improvement in the maximum respiratory capacity ($VO_{2max}$) of sportsmen solely after significant endurance exertion (80 min at 70% of their $VO_{2max}$). But in the absence of long-lasting physical exertion, taking 3 g/day n-3 LC-PUFA had no effect (Léger C L et al. Cah. Nutr. Diét, XXVII, 2, 1992). This has been confirmed elsewhere; Mickleborough T D et al., Am. J. Respir. Crit. Care Med. 168 (10), 1181-9 (2003) have shown that the daily intake of 3.2 g of EPA and 2.2 g of DHA in the form of fish oil had no effect on the pulmonary function before exertion of elite athletes.

SUMMARY OF THE INVENTION

In one aspect, the invention provides a pharmaceutical composition comprising a pharmaceutically-acceptable excipient and at least one phospholipid of the general formula (I)

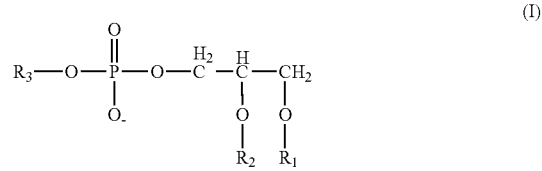

wherein one of $R_1$ or $R_2$ represents a docosahexaenoyl residue (DHA) and the other represents a saturated or unsaturated acyl residue containing 8 to 24 carbon atoms, or both $R_1$ and $R_2$ represent independently and at each occurrence a docosahexaenoyl residue (DHA); and $R_3$ represents a choline residue, a serine residue, an ethanolamine residue, an inositol residue, a glycerol residue, or hydrogen.

In certain embodiments of the invention, one of $R_1$ or $R_2$ represents a docosahexaenoyl residue (DHA) and the other represents a saturated or unsaturated acyl residue selected from a palmitate residue, a stearate residue, an oleate residue, a linoleate residue, or an arachidonate residue.

In certain embodiments of the invention, $R_3$ represents a choline residue of formula —$CH_2CH_2N^+(CH_3)_3$.

In certain embodiments of the invention, the pharmaceutical composition comprises a DHA lecithin.

In certain embodiments of the invention, the pharmaceutical composition comprises a phospholipid of the formula:

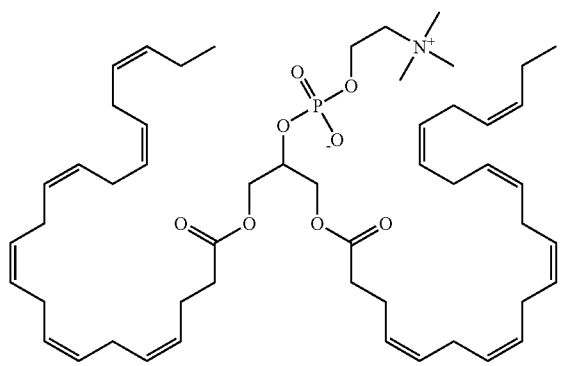

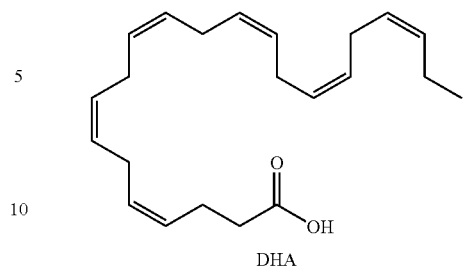

DHA

In certain embodiments of the invention, the pharmaceutical composition comprises a phospholipid of formula (I) present in partially or fully hydrolysed form.

In certain embodiments of the invention, the pharmaceutical composition is provided in a unit dose comprising an equivalent of 200 mg of DHA.

In certain embodiments of the invention, the pharmaceutical composition is provided in the form of DHA-enriched egg or DHA-enriched egg extracts.

In certain embodiments of the invention, the pharmaceutical composition is provided in a solid or liquid form selected from powder, plain or sugar-coated tablet, capsule, soft capsule, granule, lozenge, suppository, or syrup.

In certain embodiments of the invention, the pharmaceutical composition is provided in the form of a food supplement.

In certain embodiments of the invention, the pharmaceutical composition is an enteral composition.

In certain embodiments of the invention, the pharmaceutical composition is intended for the treatment and/or the prevention of respiratory failure in a patient, particularly in a human.

In other aspects, the invention provides a method for treating or preventing respiratory failure of a patient comprising administering to a patient in need of such treatment or prevention a pharmaceutical composition as described herein.

DETAILED DESCRIPTION OF THE INVENTION

The inventors have now surprisingly shown that an oral supplement of DHA alone in the form of phospholipids at a dose of less than 200 mg/day, allows people with respiratory failure, incapable in their state of performing the least of physical effort for a long duration, to improve, sometimes in a spectacular way, their ability to move. These improvements are linked to the taking of the supplement, disappearing shortly after ceasing to take it, and reappearing on its reintroduction.

In humans, nutritional supplements based on DHA in the form of phospholipids, with the aim of preventing the effects of respiratory failure, have never been described.

Thus, the present invention relates to the use of docosahexaenoic acid (DHA; C22:6 n-3) in the form of phospholipids for the preparation of composition intended for the prevention of respiratory failure.

DHA is a fatty acid from the omega-3 family comprising a carbon chain of 22 carbon atoms and 6 cis-double bonds (C22:6 n-3) with the following formula:

It should be noted that DHA is a fatty acid which has long been known for its protective role towards cardiovascular problems and depression. It is also recommended to pregnant women for the healthy development of the foetus. As a general rule, nutritionists advise the consumption of around 2 mg/kg/day to maintain well-being (Nutritional supplements advised to the French population, Agence Française pour la Sécurité Sanitaire des Aliments, TEC and DOC editions, Paris, 2001). Specific diets also exist, largely based on fish, which enable the DHA content in food to be significantly increased.

Nevertheless, food diets rich in DHA have never shown any particular effects on respiratory failure.

It is, therefore, very unexpected that the inventors have noticed that certain extracts of eggs enriched with DHA, provide a noticeable improvement in the symptoms of respiratory failure.

Moreover, it has been noted that high doses of DHA in the form of fish oils have a tendency to cause bloatedness and diarrhoea, increasing the risk of enteropathy (Burns C. P. et al., Phase I clinical study of fish oil fatty acid capsules for patients with cancer cachexia: cancer and leukemia group B, study 9473, 1999, *Clin. Cancer Res.* 5(12): 3942-3947).

Thus, the inventors have shown that doses of DHA as low as 200 mg/day are sufficient to give an improvement in the quality of life of people with respiratory failure.

Furthermore, by analysing different parameters of respiratory failure, the inventors realised that DHA-phospholipids from eggs, mainly lecithins, show properties with regard to respiratory failure that are not shown with other forms of DHA, in particular those in the form of triacylglycerides, in their ability to change the fatty acid composition in the red corpuscle membranes.

The subject of the present invention therefore concerns a pharmaceutical composition comprising a pharmaceutically-acceptable excipient and at least one phospholipid of the general formula (I)

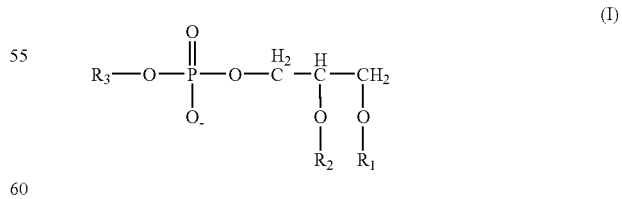

(I)

wherein one of $R_1$ or $R_2$ represents a docosahexaenoyl residue (DHA) and the other represents a saturated or unsaturated acyl residue containing 8 to 24 carbon atoms, or both $R_1$ and $R_2$ represent independently and at each occurrence a docosahexaenoyl residue (DHA); and $R_3$ represents a choline residue, a serine residue, an ethanolamine residue, an inositol residue, a glycerol residue, or hydrogen; as well as methods of treatment and prevention of respiratory failure in a patient, particularly a human, comprising administering the same.

An interesting aspect of the invention resides in the fact that the treatment or the prevention of respiratory failure only requires the administration of an equivalent dose of DHA of between 0.1 and 2.5 mg/kg/day, for an individual of average build of around 75 kg.

An equivalent dose of DHA means the quantity by mass of the DHA residue of formula II:

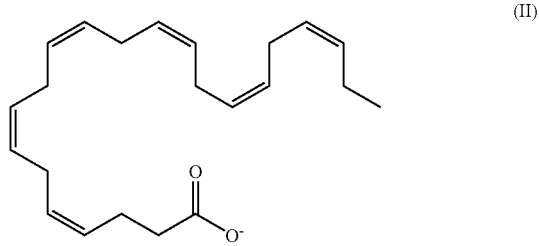

(II)

provided by the phospholipids of formula (I).

A phospholipid of formula (I) is a complex lipid formed from glycerol of which two alcohol groups are esterified by fatty acids (groups $R_1$ and $R_2$), the third being esterified by phosphoric acid, itself being linked to several compounds (group $R_3$).

Preferably, according to the invention, the docosahexaenoyl (DHA) residue is in position $R_2$.

In a particular embodiment of the invention, when one of the groups $R_1$ or $R_2$ is an acyl residue, then the acyl residue is selected from a palmitate, stearate, oleate, linoleate or arachidonate residue, but preferably is a palmitate residue.

In another particularly preferred embodiment of the invention, the group $R_3$ represents a group corresponding to choline of formula:

$$—CH_2CH_2N^+(CH_3)_3$$

Phospholipids, which are suitable according to the invention, are generally found in the form of mixtures of different types of phospholipids of formula (I), and consist particularly of DHA-lecithins, notably phosphorated lipid complexes combined with oils, or predominantly chlonic glycerophospholipids of formula (I). These lecithins are amphoteric, soluble in alcohol, precipitated by acetone and form an emulsion with water. Such lecithins are found most particularly in eggs, which can be enriched or not with DHA.

A method of obtaining DHA-lecithins, notably from eggs of birds, whose feed (diet) has been enriched with DHA, is described, e.g., in the French Pat. Appl. Publ. No. FR 2749133. The DHA lecithins prepared according to this method are particularly suitable for the purposes of use according to the invention.

A preferred embodiment of the invention therefore consists of the use of at least one phospholipid of formula (I) in which the said phospholipid is extracted from eggs, more particularly from eggs enriched with DHA.

Generally, the equivalent dose of DHA, calculated from the body mass and by day is in the range between 0.1 and 2.5 mg/kg/day and more preferably in the range between 0.3 and 2 mg/kg/day. These doses correspond respectively to an average dose of phospholipids of formula (I) calculated from the body mass and by day, in the range respectively between 1 and 70 mg/kg/day, preferably between 3.5 and 50 mg/kg/day and more preferably between 7.5 and 25 mg/kg/day (gross weight of phospholipids).

The phospholipids of formula (I) can be used as they are, that is to say substantially non-associated with other phospholipids or fatty acids. However, due to the fact that it is easier to extract these phospholipids from natural products, the said phospholipids are, more often, used in the form of complexes comprising other phospholipids and/or fatty acids.

According to the invention, the phospholipids of formula (I) can be used in the form of total or partial hydrolysates. These hydrolysates generally consist of free DHA and as necessary, other fatty acids arising from phospholipids of formula (I). Such hydrolysates are obtained by standard methods, for example, by reacting enzymes such as pancreatic phospholipase and pancreatic lipase on the phospholipids of formula (I).

The term "enteral formulation," as used herein, refers to a composition allowing for the introduction of a reagent by the digestive route. A useable enteral composition according to the invention can assume different forms, and can consist notably of a solid or liquid pharmaceutical composition in the form of a powder, plain or sugar-coated tablets, capsules, soft capsules, granules, lozenges, suppositories, syrups, etc.

Taking into account the fact that the phospholipids of formula (I) previously described show no toxicity to humans, the composition according to the invention can take the form of a food supplement. Such a food supplement is particularly recommended to improve the quality of life of people with respiratory failure, and even for prevention, before the first symptoms of the illness are noticed.

In another particular embodiment of the invention, the composition can be incorporated into a foodstuff, thus enriching it in DHA.

The example given below intends to illustrate the invention in a non-limiting way.

EXAMPLE

The effect of "phospholipid" treatment was evaluated by the administration of a dose of 140 mg/day of DHA in the form of egg yolk powder (10 g/day) containing predominantly, phospholipids in the form of DHA to individuals prone to respiratory insufficiency. It was the tendency to breathlessness that was evaluated during the transition from a resting state to a state of exertion.

State of exertion means, in the current test, the transition from a resting state to exertion proportional to the recognised capacities of the individuals. The improvement was based on the tendency to breathlessness of the individual during the state of exertion.

The placebo used consisted of soft capsules of ethyl ester of DHA (175 mg/day). The esters of fatty acids are slightly less well metabolised than triacylglyceride and phospholipid forms, hence the use of a dose 25% higher for the placebo.

The following procedure was carried out:

5 individuals, 3 women and 2 men, aged between 60 and 83 years, with weights of between 72 and 109 kg and heights of between 145 and 175 cm, received a placebo for 3 weeks. At the end of this supplementation, a check-up of their respiratory insufficiency was carried out.

Then, the 5 individuals received 3 weeks of "phospholipid" treatment and another check-up of their respiratory insufficiency was carried out.

Then, the supplementation of the DHA phospholipid was stopped for 6 weeks at the end of which, a further check-up was performed.

Then, the supplementation was resumed for 3 weeks and a check-up was carried out.

The table below summarises the severity of the respiratory insufficiency of the people before and after supplementation, with the placebo or with the composition according to the invention.

| Patient | Dyspnoea | | | | | |
| --- | --- | --- | --- | --- | --- | --- |
| | Before treatment | | After treatment | | | |
| | | | Placebo | | "phospholipids" | |
| | At rest | Upon exertion | At rest | Upon exertion | At rest | Upon exertion |
| A | ++ | ++ | ND | | + | + |
| B | + | ++ | + | ++ | 0 | + |
| C | 0 | + | 0 | + | 0 | 0 |
| D | + | ++ | + | ++ | 0 | 0 |
| E | + | ++ | + | ++ | 0 | 0 |

Legend: 0: no respiratory insufficiency; +: mild respiratory insufficiency; ++: severe respiratory insufficiency; ND: not determined These results show a decrease, even a disappearance, of the tendency to breathlessness of people having received a supplement of DHA phospholipids, whether it be after supplementation in a resting state or in a state of exertion.

These results point towards a DHA phospholipid supplementation improving the quality of life of those with respiratory failure.

It is interesting to note that when the supplementation of DHA phospholipids is stopped, patients revert to their condition as it was before taking the supplements and when supplementation is recommenced, the improvements noticed before stopping the supplements are reproduced. The effect of DHA phospholipid supplementation is therefore transitory and cannot be considered a therapeutic treatment.

What is claimed is:

1. A method for treating respiratory failure of a patient comprising administering to a patient in need of such treatment a pharmaceutical composition comprising a pharmaceutically-acceptable excipient and at least one phospholipid of the general formula (I)

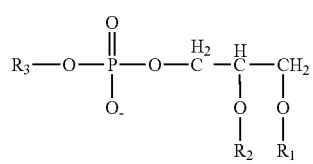

wherein
one of $R_1$ or $R_2$ represents a docosahexaenoyl (DHA) and the other represents a saturated or unsaturated acyl group containing 8 to 24 carbon atoms, or both $R_1$ and $R_2$ represent independently and at each occurrence a docosahexaenoyl group (DHA); and $R_3$ represents a choline group, a serine group, an ethanolamine group, an inositol group, a glycerol group, or hydrogen.

2. The method of claim 1, wherein one of $R_1$ or $R_2$ represents a docosahexaenoyl group (DHA) and the other represents a saturated or unsaturated acyl group selected from a palmitate group, a stearate group, an oleate group, a linoleate group, or an arachidonate group.

3. The method of claim 2, wherein $R_3$ represents a choline group of formula —$CH_2CH_2N^+(CH_3)_3$.

4. The method of claim 1, wherein the phospholipid comprises a DHA lecithin.

5. The method of claim 1, wherein the phospholipid of formula (I) is present in partially or fully hydrolysed form.

6. The method of claim 1, wherein the pharmaceutical composition is provided in a unit dose form comprising an equivalent of 200 mg of DHA.

7. The method of claim 1, wherein the pharmaceutical composition is provided in the form of DHA-enriched egg or DHA-enriched egg extracts.

8. The method of claim 1, wherein the pharmaceutical composition is provided in a solid or liquid form selected from powder, plain or sugar-coated tablet, capsule, soft capsule, granule, lozenge, suppository, or syrup.

9. The method of claim 1, wherein the pharmaceutical composition is provided in the form of a food supplement.

10. The method of claim 1, wherein $R_1$ and $R_2$ each represents independently and at each occurrence a docosahexaenoyl group having all cis double bonds.

11. A method for treating respiratory failure of a patient comprising administering to a patient in need of such treatment a pharmaceutical composition comprising: (a) a pharmaceutically-acceptable excipient and (b) DHA-enriched egg or DHA-enriched egg extracts.

12. A method for treating respiratory failure of a patient comprising administering to a patient in need of such treatment a pharmaceutical composition comprising (a) a pharmaceutically-acceptable excipient and (b) DHA-enriched egg or DHA-enriched egg extracts, wherein said DHA-enriched egg or said DHA-enriched egg extracts comprise DHA enriched egg lecithin.

13. A method for treating respiratory failure of a patient comprising administering to a patient in need of such treatment a pharmaceutical composition comprising (a) a pharmaceutically-acceptable excipient and (b) DHA-enriched egg or DHA-enriched egg extracts, wherein said DHA-enriched egg or said DHA-enriched egg extracts comprise egg yolk powder.

14. The method of claim 1, wherein when the pharmaceutical composition comprises one and only one phospholipid of the general formula (I), said phospholipid is not 1-oleoyl-2-docosahexaenoyl-sn-glycero-3-phosphorylcholine.

15. The method of claim 14, wherein respiratory failure comprises respiratory insufficiency and does not comprise asthma.

* * * * *